United States Patent
Grothe et al.

(10) Patent No.: US 11,266,437 B2
(45) Date of Patent: Mar. 8, 2022

(54) DRIVE SHAFT WITH METALLIC INNER LAYER AND POLYMER JACKET

(71) Applicant: Cardiovascular Systems, Inc., St. Paul, MN (US)

(72) Inventors: Preston L. Grothe, Maple Grove, MN (US); Matthew D. Cambronne, North Oaks, MN (US); Joseph P. Higgins, Minnetonka, MN (US); Jeffrey R. Stone, Minnetonka, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 218 days.

(21) Appl. No.: 16/807,669

(22) Filed: Mar. 3, 2020

(65) Prior Publication Data
US 2020/0323552 A1     Oct. 15, 2020

Related U.S. Application Data (60) Provisional application No. 62/834,023, filed on Apr. 15, 2019.

(51) Int. Cl.
*A61B 17/3207* (2006.01)
*A61B 17/3205* (2006.01)
*A61B 17/32* (2006.01)

(52) U.S. Cl.
CPC ......... *A61B 17/320758* (2013.01); *A61B 2017/320004* (2013.01); *A61B 2017/320032* (2013.01); *A61B 2217/007* (2013.01)

(58) Field of Classification Search
CPC ...... A61B 17/320758; A61B 17/32002; A61B 17/00234
See application file for complete search history.

(56) References Cited

U.S. PATENT DOCUMENTS

| | | |
|---|---|---|
| 5,669,920 A | 9/1997 | Conley et al. |
| 8,109,954 B2 | 2/2012 | Shturman |

(Continued)

FOREIGN PATENT DOCUMENTS

| | | |
|---|---|---|
| WO | 2018052121 | 3/2018 |

OTHER PUBLICATIONS

Notification Concerning Transmittal of International Preliminary Report on Patentability and International Preliminary Report on Patentability issued in related application No. PCT/US2020/21084, dated Oct. 28, 2021.

(Continued)

*Primary Examiner* — Tuan V Nguyen
(74) *Attorney, Agent, or Firm* — Barnes & Thornburg LLP; Jeffrey R. Stone (57) ABSTRACT

Various embodiments of devices and systems comprising a driveshaft for use in high-speed rotational medical procedures; e.g., atherectomy, are disclosed. Generally, the driveshaft is configured for transferring torque and activating rotation of a tool attached thereto, e.g., an abrading head, and is covered by a polymer jacket. In certain embodiments, the polymer jacket is allowed to rotate in response to the rotation of the drive shaft such that the polymer jacket is not fixed at its proximal end. Various embodiments of the drive shaft may include proximal and/or distal stops that enable the polymer jacket to move longitudinally between the stops, in embodiments comprising proximal and distal stops, or to the distal stop in embodiments comprising only a distal stop. Various embodiments of the devices and systems described herein optionally may include a metallic inner liner within the drive shaft, in addition to or instead of a polymer jacket.

12 Claims, 4 Drawing Sheets

(56) References Cited

U.S. PATENT DOCUMENTS 9,554,823 B2     1/2017   Weber et al.
2005/0288695 A1   12/2005   Jenson et al.
2012/0109171 A1*   5/2012   Zeroni ........... A61B 17/320758
                                                             606/159
2018/0317952 A1*   11/2018   Jamous ............. A61M 25/0082

OTHER PUBLICATIONS

International Search Report and Written Opinion issued in related PCT/US2020/21084, dated Jun. 3, 2020.

* cited by examiner

DRIVE SHAFT WITH METALLIC INNER LAYER AND POLYMER JACKET

CROSS-REFERENCE TO RELATED APPLICATIONS

This application claims the benefit of U.S. Provisional Application No. 62/834,023, filed Apr. 15, 2019 and entitled DRIVE SHAFT WITH METALLIC INNER LAYER AND POLYMER JACKET, the entirety of which is hereby incorporated by reference.

STATEMENT REGARDING FEDERALLY SPONSORED RESEARCH OR DEVELOPMENT

Not Applicable

BACKGROUND OF THE INVENTION

Field of the Invention

The disclosure relates to drive shafts used in medical device procedures. More specifically, the disclosure relates to drive shafts used in rotational atherectomy and thrombectomy procedures.

Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. For non-calcified lesions, balloon angioplasty most often is used alone to open the artery, and stents often are placed to maintain patency of the opened artery. Studies have shown, however, that a significant percentage of patients who have undergone balloon angioplasty and had a stent placed in an artery experience stent restenosis, which is blockage of the stent that most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patency of the artery.

Several kinds of rotational atherectomy devices have been developed for attempting to remove stenotic material. Such devices generally include a drive shaft on which an abrading head is disposed and a handle comprising a rotational drive mechanism and coupled to a proximal portion of the drive shaft. Known drive shafts for use with rotational atherectomy devices generally comprise metallic wire turns, typically of stainless steel metallic construction, and may be covered by a polymer coating or a polymer jacket that is fixed longitudinally relative to the drive shaft. The polymer coating or polymer jacket may help contain fluid within and/or around the drive shaft during rotation and may, to some extent, help the drive shaft to maintain a working diameter that is as close as possible to its resting diameter during rotation of the drive shaft. The polymer coating will rotate with the drive shaft while typically, the polymer jacket does not rotate. In other words, in atherectomy devices comprising a polymer jacket covering the drive shaft, the drive shaft may rotate within the polymer jacket while the polymer jacket remains stationary relative to the handle.

Although a polymer jacket, fixed longitudinally in position as in such known systems, may help a rotating drive shaft maintain a diameter close to its resting diameter during high-speed rotation better than systems that do not include a polymer jacket, Applicant has found that such known polymer jackets can be improved upon. For example, the known fixed-position polymer jackets may not adequately mitigate radial excursions of the drive shaft and other issues that may arise during high-speed rotation of the drive shaft, such as unwanted vibration and/or standing waves in the drive shaft during high-speed rotation. Radial excursions of the drive shaft, unwanted vibrations, and/or standing waves in the drive shaft during high-speed rotation may deflect the abrading head from its intended path of travel, which in turn may reduce the efficacy of the abrading head in removing occlusive material and/or contribute to complications caused by uncontrolled contact of the abrading head with the vessel wall.

Accordingly, a rotational medical device (e.g., rotational atherectomy device) including a drive shaft and polymer jacket configured to address these issues is desirable. Such a device would provide improved performance relative to known rotational medical devices such as by improving the efficacy of rotational procedures and reducing the associated risk of complications. Moreover, Applicant has found that, in some embodiments, a smooth metallic inner layer may be used to provide improved performance of a rotational medical device.

Various embodiments of the present invention address these, inter alia, issues. It should be noted that such issues may arise in devices configured for use rotational procedures other than atherectomy, where the issues are likewise addressed by the various embodiments of the present invention.

Moreover, we provide disclosure of the following patents and applications, each of which are assigned to Cardiovascular Systems, Inc., and incorporated herein in their entirety, each of which may comprise systems, methods and/or devices that may be used with various embodiments of the presently disclosed subject matter:

U.S. Pat. No. 9,468,457, "ATHERECTOMY DEVICE WITH ECCENTRIC CROWN";

U.S. Pat. No. 9,439,674, "ROTATIONAL ATHERECTOMY DEVICE WITH EXCHANGEABLE DRIVE SHAFT AND MESHING GEARS";

U.S. Pat. No. 9,220,529, "ROTATIONAL ATHERECTOMY DEVICE WITH ELECTRIC MOTOR";

U.S. Pat. No. 9,119,661, "ROTATIONAL ATHERECTOMY DEVICE WITH ELECTRIC MOTOR";

U.S. Pat. No. 9,119,660, "ROTATIONAL ATHERECTOMY DEVICE WITH ELECTRIC MOTOR";

U.S. Pat. No. 9,078,692, "ROTATIONAL ATHERECTOMY SYSTEM";

U.S. Pat. No. 6,295,712, "ROTATIONAL ATHERECTOMY DEVICE";

U.S. Pat. No. 6,494,890, "ECCENTRIC ROTATIONAL ATHERECTOMY DEVICE";

U.S. Pat. No. 6,132,444, "ECCENTRIC DRIVE SHAFT FOR ATHERECTOMY DEVICE AND METHOD FOR MANUFACTURE";

U.S. Pat. No. 6,638,288, "ECCENTRIC DRIVE SHAFT FOR ATHERECTOMY DEVICE AND METHOD FOR MANUFACTURE";

U.S. Pat. No. 5,314,438, "ABRASIVE DRIVE SHAFT DEVICE FOR ROTATIONAL ATHERECTOMY";

U.S. Pat. No. 6,217,595, "ROTATIONAL ATHERECTOMY DEVICE";

U.S. Pat. No. 5,554,163, "ATHERECTOMY DEVICE";

U.S. Pat. No. 7,507,245, "ROTATIONAL ANGIOPLASTY DEVICE WITH ABRASIVE CROWN";

U.S. Pat. No. 6,129,734, "ROTATIONAL ATHERECTOMY DEVICE WITH RADIALLY EXPANDABLE PRIME MOVER COUPLING";

U.S. patent application Ser. No. 11/761,128, "ECCENTRIC ABRADING HEAD FOR HIGH-SPEED ROTATIONAL ATHERECTOMY DEVICES";

U.S. patent application Ser. No. 11/767,725, "SYSTEM, APPARATUS AND METHOD FOR OPENING AN OCCLUDED LESION";

U.S. patent application Ser. No. 12/130,083, "ECCENTRIC ABRADING ELEMENT FOR HIGH-SPEED ROTATIONAL ATHERECTOMY DEVICES";

U.S. patent application Ser. No. 12/363,914, "MULTI-MATERIAL ABRADING HEAD FOR ATHERECTOMY DEVICES HAVING LATERALLY DISPLACED CENTER OF MASS";

U.S. patent application Ser. No. 12/578,222, "ROTATIONAL ATHERECTOMY DEVICE WITH PRE-CURVED DRIVE SHAFT";

U.S. patent application Ser. No. 12/130,024, "ECCENTRIC ABRADING AND CUTTING HEAD FOR HIGH-SPEED ROTATIONAL ATHERECTOMY DEVICES";

U.S. patent application Ser. No. 12/580,590, "ECCENTRIC ABRADING AND CUTTING HEAD FOR HIGH-SPEED ROTATIONAL ATHERECTOMY DEVICES";

U.S. patent application Ser. No. 29/298,320, "ROTATIONAL ATHERECTOMY ABRASIVE CROWN";

U.S. patent application Ser. No. 29/297,122, "ROTATIONAL ATHERECTOMY ABRASIVE CROWN";

U.S. patent application Ser. No. 12/466,130, "BIDIRECTIONAL EXPANDABLE HEAD FOR ROTATIONAL ATHERECTOMY DEVICE"; and U.S. patent application Ser. No. 12/388,703, "ROTATIONAL ATHERECTOMY SEGMENTED ABRADING HEAD AND METHOD TO IMPROVE ABRADING EFFICIENCY".

BRIEF SUMMARY OF THE INVENTION

Various embodiments of rotational devices comprising a driveshaft for use in high-speed rotational medical procedures; e.g., atherectomy, are disclosed. Generally, the driveshaft is configured for transferring torque and activating rotation of a tool attached thereto, e.g., an abrasive element (which also may be described herein as an "abrading head"), and is covered by a polymer jacket. In certain embodiments, the polymer jacket is not fixed at its proximal end and thus is allowed to rotate in response to the rotation of the drive shaft. Various embodiments of the drive shaft may include proximal and/or distal outer stop(s) that enable the polymer jacket to move longitudinally between the stops, in embodiments comprising proximal and distal outer stops, or to the distal outer stop in embodiments comprising only a distal stop. Various embodiments of the devices and systems described herein optionally may comprise a metallic inner liner within the drive shaft, in addition to or instead of a polymer jacket. In certain embodiments, the metallic inner liner is not fixed at its proximal end and thus is allowed to rotate in response to the rotation of the drive shaft. Some embodiments that include a metallic inner liner also may include proximal and/or distal inner stop(s) that enable the metallic inner liner to move longitudinally therebetween, in embodiments comprising proximal and distal inner stops, or to the distal inner stop in embodiments comprising only a distal stop.

Embodiments of the present invention may address problems associated with known rotational devices by providing a rotatable, longitudinally movable polymer jacket surrounding a drive shaft, which minimizes unwanted radial excursions of the drive shaft and dampens vibrations better than the fixed polymer jackets of known rotational devices. Additionally, or alternatively, features of the embodiments of the present invention may reduce or eliminate unwanted vibration and/or standing waves in the drive shaft during high-speed rotation better than the fixed polymer jackets of known rotational devices.

One embodiment is a medical device comprising: a rotational drive shaft; and a polymer jacket partially surrounding the rotational drive shaft, wherein the polymer jacket does not rotate in response to rotation of the rotational drive shaft and wherein the polymer jacket is fixed in longitudinal position.

A further embodiment is a medical device comprising: a rotational drive shaft; and a polymer jacket partially surrounding the rotational drive shaft, wherein the polymer jacket is configured to move rotationally and/or longitudinally independently of the drive shaft in response to rotation of the drive shaft.

A further embodiment is a rotational atherectomy device comprising: a prime mover with a prime mover drive shaft operationally connected thereto; a rotational drive shaft; an abrading head disposed on the rotational drive shaft and a polymer jacket partially surrounding the rotational drive shaft, wherein a distal end of the polymer jacket is proximal to the abrading head, wherein the polymer jacket is configured to move rotationally and/or longitudinally independently of the drive shaft in response to rotation of the drive shaft.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

DETAILED DESCRIPTION OF THE INVENTION

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention. It further should be understood that although one or more of the embodiments described herein are described or illustrated as including each of a proximal stop, a distal stop, and a metal liner, embodiments comprising fewer than all of these features are also contemplated and within the scope of this disclosure.

FIGS. 1-9 illustrate various embodiments of known devices and devices of the present invention. Though these embodiments are illustrated separately, it will be understood by the skilled artisan that aspects of one or more of the illustrated embodiments may be combined.

Figure 1:
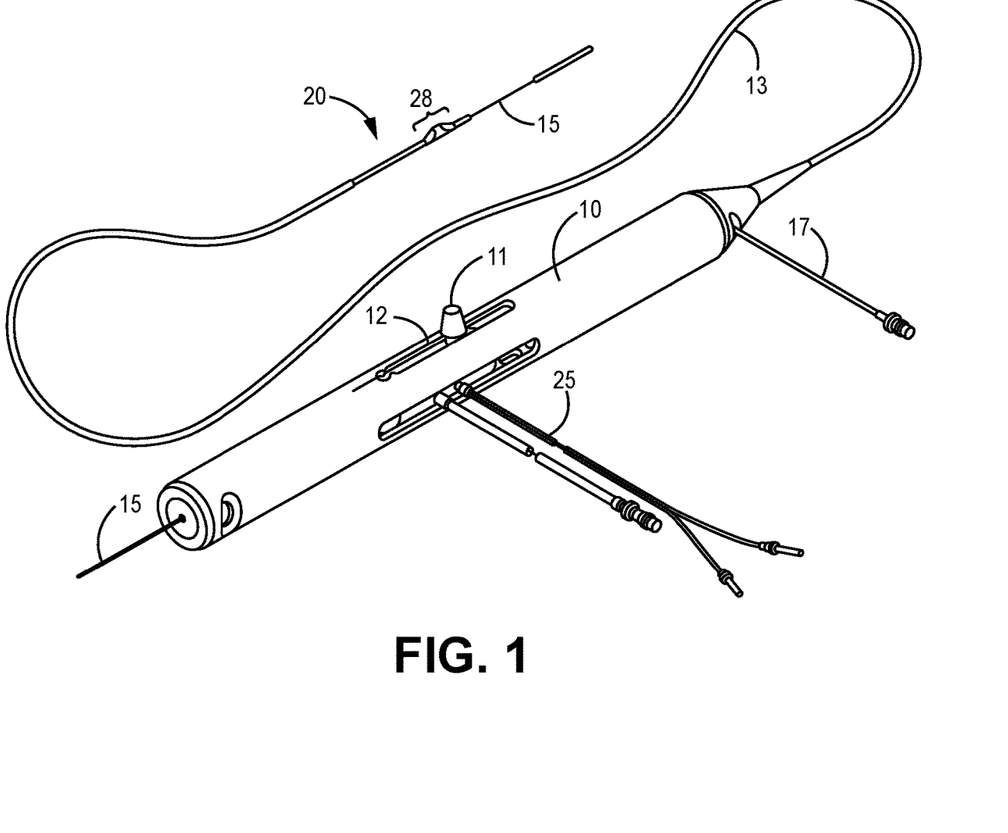
FIG. 1 is a perspective view of one embodiment of a known rotational atherectomy device and system.

FIG. 1 illustrates one known embodiment of a rotational atherectomy device that may incorporate the present invention. The device includes a handle portion 10, an elongated, flexible drive shaft 20 having an enlarged abrading head 28, and an elongated catheter 13 extending distally from the handle portion 10. The drive shaft 20 is constructed from helically coiled wire as is known in the art and the abrading head 28 is fixedly attached thereto. Known drive shafts such as drive shaft 20 are manufactured from a multi-filar wound coil, where the coil may comprise any suitable metallic material. The inherent construction of this known coil allows for spaces between the filars. These spaces allow fluid, e.g., saline and/or water or other fluid, to pass through to the inner diameter of the drive shaft coil in order to provide cooling and/or lubrication effects to the interface of the drive shaft coil and the guidewire 15.

Generally, in this known construction, a coupler (typically comprising a solid metallic tube) is attached to the proximal end of the coiled drive shaft and to the drive shaft of the handle portion 10, wherein the drive shaft of the handle portion 10 is driven by a prime mover, thereby providing a connection between the prime mover, e.g., a turbine or electric motor, and the drive shaft 20. However, other suitable drive shaft constructions may be used, to the extent compatible with the embodiments of this disclosure, without departing from the from the scope and spirit of the invention.

Continuing with reference to FIG. 1, the catheter 13 has a lumen in which most of the length of the drive shaft 20 is disposed, except for the enlarged abrading head 28 and a short section distal to the abrading head 28. The drive shaft 20 also defines an inner lumen, permitting the drive shaft 20 to be advanced and rotated over the guidewire 15. A fluid supply line 17 may be provided for introducing a cooling and lubricating solution (typically saline or another biocompatible fluid) into the catheter 13.

The handle portion 10 desirably contains a turbine (or similar rotational drive mechanism) for rotating the drive shaft 20 at high speeds. The handle portion 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20. The handle portion 10 also desirably includes a control knob 11 for advancing and retracting the turbine and drive shaft 20 with respect to the catheter 13 and the body of the handle portion 10.

Figure 2:
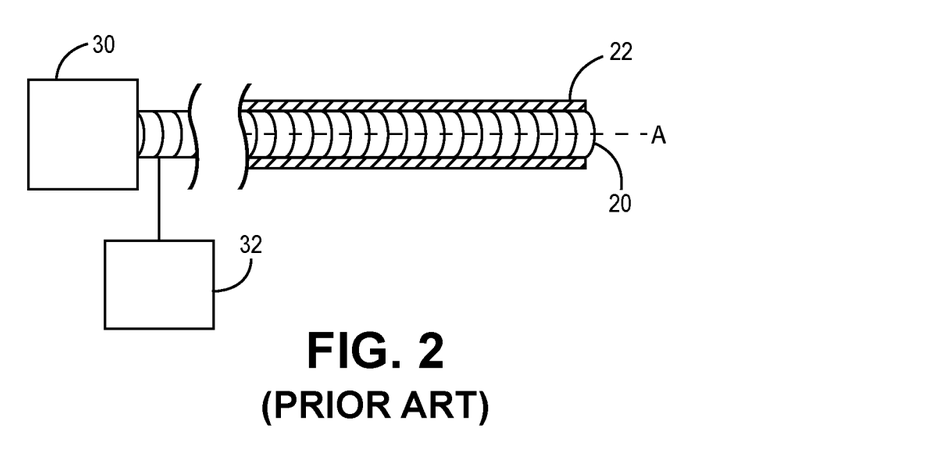
FIG. 2 is a partial schematic diagram and partial longitudinal cross-sectional view of one known embodiment of a rotational medical device and system, the cross-section taken substantially parallel to longitudinal axis A.

FIG. 2 is a partial schematic diagram and partial longitudinal cross-sectional view of one known embodiment of a rotational medical device, the cross-section taken substantially parallel to longitudinal axis A. It should be noted that any one or more of the features, functions, and advantages described herein with respect to the rotational medical device of FIG. 1 optionally may be included in the rotational medical device of FIG. 2 and vice versa. It also should be noted that like reference numerals denote substantially-like features across the rotational medical devices of FIGS. 1 and 2; e.g., the drive shaft 20 may be substantially the same in the rotational medical devices of FIGS. 1 and 2.

The rotational medical device shown in FIG. 2 comprises a drive shaft 20 comprising wire or metallic turns operatively connected to a prime mover 30 such as a turbine, pneumatic device or electric motor. A fluid reservoir 32 is operatively and fluidly connected with the system and an outer polymer jacket 22 is provided, fixed in longitudinal position at the proximal end of the drive shaft 20 and extending distally to the distal end of the wire turns of the drive shaft 20, wherein the polymer jacket 22 and the wire turns of the drive shaft 20 terminate at generally the same location. That is, the polymer jacket 22 covers all of the drive shaft 20 in the embodiment of FIG. 2. The drive shaft 20 rotates independently of, and within, the polymer jacket 22. Generally, the polymer jacket 22 helps contain fluid within and/or around the drive shaft 20 during rotation and further assists the drive shaft 20 to maintain a working diameter that is as close as possible to its resting diameter. Stated differently, the polymer jacket 22 aids in minimizing unwanted radial excursions by the flexible wire turns of the drive shaft 20, keeping the drive shaft 20 as aligned with a resting, nominal rotational axis A as possible.

Figure 3:
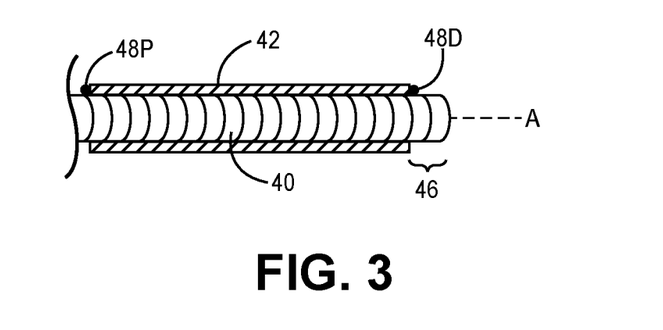
FIG. 3 is a longitudinal cross-sectional view of one embodiment of the present invention, the cross-section taken substantially parallel to longitudinal axis A.

FIG. 3 is a longitudinal cross-sectional view of one embodiment of the present invention, the cross-section taken substantially parallel to longitudinal axis A. In FIG. 3, the prime mover 30 and fluid reservoir 32 elements illustrated in FIG. 2 are omitted, but may be considered part of the system of FIG. 3. A drive shaft 40 comprising metallic wire turns is provided and partially covered by an outer polymer jacket 42 which is fixed at its proximal end. One or more features of the drive shaft 40 and the polymer jacket 42 may be substantially similar to the corresponding features of the drive shaft 20 and the polymer jacket 22 of the embodiment of FIG. 2, such as the wire turns of the drive shaft 20 and/or the composition of the materials from which the drive shaft 20 and the polymer jacket 22 are formed. The polymer jacket 42 does not rotate, and so the drive shaft 40 rotates independently within the polymer jacket 42. The embodiment of FIG. 3 differs from the embodiment of FIG. 2 in that a distal section 46 of the drive shaft 40 is exposed, uncovered by the polymer jacket 42. This distal section 46 may comprise a tool, such as an atherectomy crown; e.g., an abrading head (not shown), or other tool.

Alternatively, the polymer jacket 42 may not be fixed at its proximal end. In this alternative embodiment of FIG. 3, the polymer jacket 42 is allowed to rotate in response to the rotation of the drive shaft 40, though the polymer jacket 42 and the drive shaft 40 are not connected per se. The drive shaft 40 may comprise proximal and distal atraumatic stops 48P and 48D which may comprise smoothed atraumatic elevations above the outer surface of the drive shaft 40. The polymer jacket 42 is thus restricted longitudinally between the stops 48P and 48D, which may prevent any longitudinal movement of the polymer jacket 42 or may allow some longitudinal movement, depending on the distance between the stops 48P and 48D relative to the length of the polymer jacket 42. Still more alternatively, only a distal stop 48D may be provided, wherein the polymer jacket 42 is free to move distally to the distal stop 48D. Still more alternatively, proximal stop 48P and/or distal stop 48D each may comprise more than one elevation, with the several proximal elevations and/or the several distal elevations radially spaced from one another about the circumference of the corresponding proximal or distal section of the drive shaft 40. In all cases of this embodiment, the polymer jacket 42 is free to rotate during rotation of the drive shaft 40, but doesn't rotate necessarily at the same speed as the drive shaft 40.

This arrangement in which the polymer jacket 42 is free to rotate during rotation of the drive shaft 40 assists in, as discussed above, holding the outer diameter of the drive shaft 40 to a working diameter that approximates its resting diameter during rotation, adding a further resonance reduction or mitigation feature when the polymer jacket 42 is properly positioned between proximal and distal stops 48P and 48D, with or without longitudinal movement of the polymer jacket 42 therebetween. For example, allowing the polymer jacket 42 to rotate and longitudinally translate between proximal and distal stops 48P and 48D allows the polymer jacket 42 to rotate and/or longitudinally translate to assist in reducing any unwanted vibration and/or standing wave issues that may arise during high-speed rotation of the drive shaft 40. That is, allowing the polymer jacket 42 to rotate and longitudinally translate between proximal and distal stops 48P and 48D allows the polymer jacket 42 to rotate and/or slide to a natural position to help minimize or eliminate these potential issues.

In addition to the above benefits, the arrangement of FIG. 3 provides additional stability and support for the guidewire (not shown but well known to the skilled artisan; e.g., guidewire 15 shown in FIG. 1) that may extend through the lumen of the drive shaft 40. It is known that vibrations and other forces may adversely affect guidewires in addition to drive shafts, particularly at the distal ends thereof. In dampening the radial excursions of the drive shaft 40, the polymer jacket 42 also works to dampen vibrations and other forces imparted to the guidewire in known devices.

Figure 4:
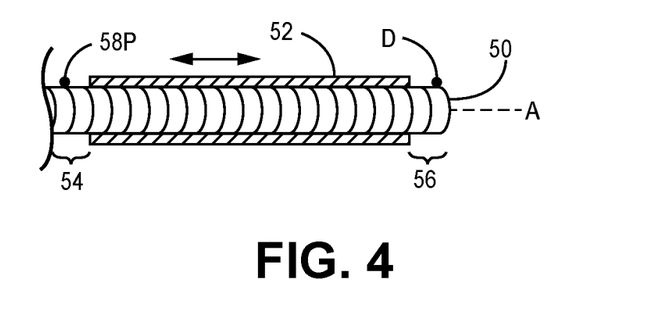
FIG. 4 is a longitudinal cross-sectional view of another embodiment of the present invention, the cross-section taken substantially parallel to longitudinal axis A.

FIG. 4 is a longitudinal cross-sectional view of another embodiment of the present invention, the cross-section taken substantially parallel to longitudinal axis A. Specifically, the embodiment of FIG. 4 is a variation of the embodiment of FIG. 3. A drive shaft 50 comprising metallic wire turns and proximal and distal stops 58P and 58D is provided and partially covered by a polymer jacket 52, leaving proximal section 54 and distal section 56 of the drive shaft 50 exposed. One or more features and advantages of the drive shaft 50, proximal and distal stops 58P, 58D, and the polymer jacket 52 may be substantially similar to the corresponding features and advantages of the drive shaft 40, stops 48P and 48D, and the polymer jacket 42 of the embodiments of FIG. 3. FIG. 4 shows the proximal and distal stops 58P and 58D spaced at a distance that is greater than the longitudinal length of the polymer jacket 52, thus allowing a predetermined length of longitudinal travel for the polymer jacket 52 to move in response to the rotation and related radial movements of the drive shaft 50, thus providing the same benefits to the drive shaft 50 and a guidewire as discussed above.

Figure 5:
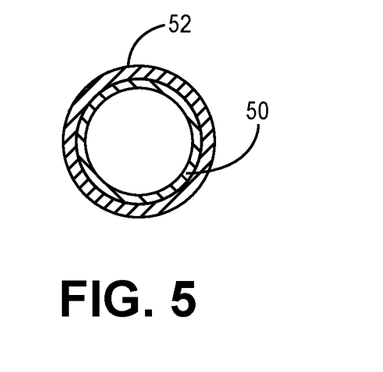
FIG. 5 is an axial cross-sectional view of the embodiments of FIGS. 3 and 4, the cross-section taken substantially perpendicular to longitudinal axis A.

FIG. 5 is an axial cross-sectional view of the embodiments of FIGS. 3 and 4, the cross-section taken substantially perpendicular to longitudinal axis A. As shown in FIG. 5, the outer polymer jacket 52 surrounds the inner wire turns of the drive shaft 50. A small circumferential space (not shown) may be defined between the drive shaft 50 and the polymer jacket 52, which may enable independent rotation of the drive shaft 50 and the polymer jacket 52.

FIGS. 6-9 illustrate various embodiments of the rotational medical devices of this disclosure in which a rotational medical device includes a smooth metal liner positioned inside a drive shaft. As described below, a metal liner may be used with, or without, a polymer jacket. When used with a polymer jacket, both the polymer jacket and the metal liner optionally may be fixed longitudinally and not connected with the drive shaft so that both the polymer jacket and the metal liner either do not rotate, or may be configured so that one or both of the polymer jacket and the metal liner rotate independently of the drive shaft.

Figure 6:
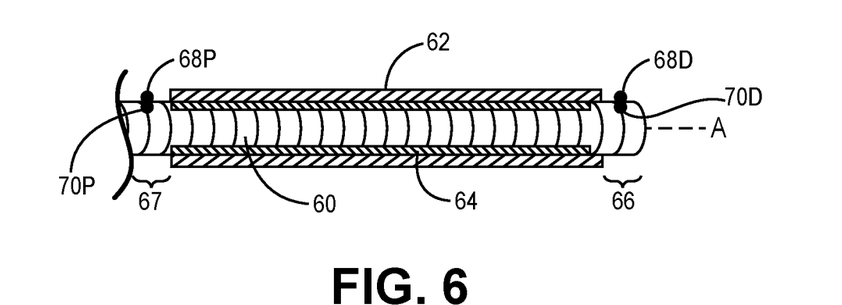
FIG. 6 is a longitudinal cross-sectional view of another embodiment of the present invention, the cross-section taken substantially parallel to longitudinal axis A.

FIG. 6 is a longitudinal cross-sectional view of another embodiment of the present invention, the cross-section taken substantially parallel to longitudinal axis A. A drive shaft 60 comprising metallic wire turns is provided and partially covered by a polymer jacket 62 such that a distal section 66 and a proximal section 67 of the drive shaft 60 are exposed. Drive shaft 60 comprises proximal and distal stops 68P and 68D. One or more features and advantages of the drive shaft 60, stops 68P and 68D, and the polymer jacket 62 may be substantially similar to the corresponding features and advantages of the drive shafts, stops, and polymer jackets of the embodiments of FIGS. 3-5. The embodiment of FIG. 6 adds a smooth metal liner 64 inside the wire turns of the drive shaft 60 to the embodiment of FIGS. 4 and 5.

The smooth metal liner 64 is flexible and is not attached to the drive shaft 60. As shown in FIG. 6, the drive shaft 60 further comprises inner proximal and distal stops 70P and 70D. Alternatively, the inner stop of drive shaft 60 may comprise only distal inner stop 70D. Inner stops 70P and 70D comprise elevations extending from an inner surface of the drive shaft 60 radially inward into the lumen defined by the drive shaft 60. In some cases, inner proximal stop 70P and/or inner distal stop 70D each may comprise more than one elevation, with the several proximal elevations and/or several distal elevations radially spaced from one another about the inner circumference of the corresponding proximal section 67 or distal section 66 of the drive shaft 60. In any such cases, the metal liner 64 is free to move within the drive shaft 60 between inner proximal and/or distal stops 70P and 70D, or between a proximal end of the drive shaft 60 and inner distal stop 70D, in a manner similar to that described above in connection with the polymer jackets and drive shafts of the embodiments of FIGS. 3-5. Metal liner 64 therefore is allowed to move longitudinally within a predetermined distance. If both proximal and distal stops inner 70P and 70D are used, then the distance between proximal and distal stops 70P and 70D may be greater than, or be equal to, the length of the metal liner 64 to define a desired longitudinal length of travel of the metal liner 64.

The metal liner 64 will help prevent fluid movement into/out of the lumen defined by the drive shaft 60 and will also provide benefits related to those described above with respect to the rotatable/longitudinally translatable polymer jackets regarding minimization of resonance, vibrations and the like, thus helping to maintain the integrity of the drive shaft 60 as well as a guidewire that will translate and/or rotate within, and relative to, the metal liner 64. In some embodiments, the metal liner 64 may have a stiffness that differs from (e.g., is greater than) a stiffness of the polymer jacket 62 and/or other polymer jackets described above such as to provide a desired amount of flexibility to the device including the metal liner 64.

Figure 7:
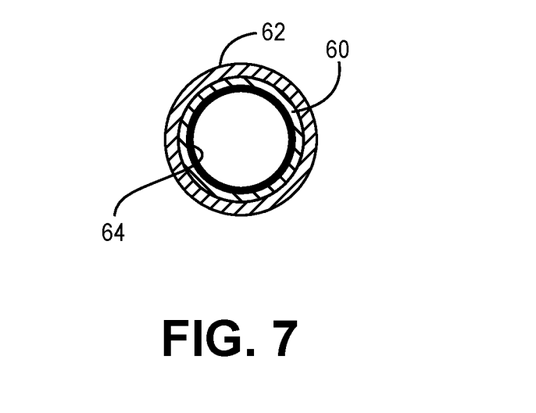
FIG. 7 is an axial cross-sectional view of the embodiment of FIG. 6, the cross-section taken substantially perpendicular to longitudinal axis A.

FIG. 7 is an axial cross-sectional view of the embodiment of FIG. 6, the cross-section taken substantially perpendicular to longitudinal axis A. As shown in FIG. 7, the outer polymer jacket 62 surrounds the inner wire turns of the drive shaft 60. A small circumferential space (not shown) may be defined between the metal liner 64 and the drive shaft 60, which may enable independent rotation of the drive shaft 60 and the metal liner 64. A small circumferential space (not shown) may be defined between the drive shaft 60 and the polymer jacket 62, which may enable independent rotation of the drive shaft 60 and the polymer jacket 62.

Figure 8:
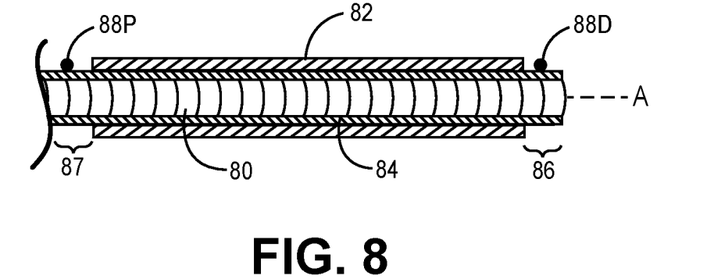
FIG. 8 is a longitudinal cross-sectional view of another embodiment of the present invention, the cross-section taken substantially parallel to longitudinal axis A.

FIG. 8 is a longitudinal cross-sectional view of another embodiment of the present invention, the cross-section taken substantially parallel to longitudinal axis A. A drive shaft 80 comprising metallic wire turns is provided and partially covered by a polymer jacket 82 such that a distal section 86 and a proximal section 87 of the drive shaft 60 are exposed. Drive shaft 80 comprises proximal and distal stops 88P and 88D. One or more features and advantages of the drive shaft 80, stops 88P and 88D, and the polymer jacket 82 may be substantially similar to the corresponding features and advantages of the drive shafts and polymer jackets of the embodiments of FIGS. 3-5. The embodiment of FIG. 8 adds a smooth metal liner 84 inside the wire turns of the drive shaft 80 to the embodiment of FIGS. 4 and 5.

The smooth metal liner 84 is flexible and may be fixed at its proximal end. Unlike the embodiment of FIG. 6, the drive shaft 80 does not comprise inner proximal and/or distal stops to allow longitudinal travel of the metal liner 84 therebetween. In cases in which the metal liner 84 is fixed at its proximal end, the metal liner 84 does not rotate, and so the drive shaft 80 and polymer jacket 82 rotate independently over the metal liner 84. Alternatively, the smooth metal liner 84 may not be fixed at its proximal end. In such cases, the metal liner 84 is free to rotate within the drive shaft 80 during rotation of the drive shaft 80.

Figure 9:
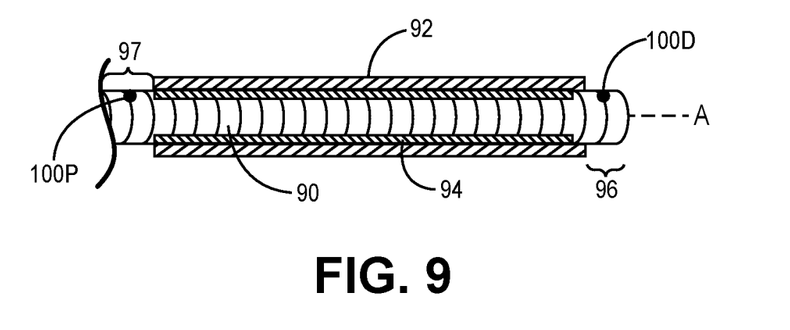
FIG. 9 is a longitudinal cross-sectional view of another embodiment of the present invention, the cross-section taken substantially parallel to longitudinal axis A.

FIG. 9 is a longitudinal cross-sectional view of another embodiment of the present invention, the cross-section taken substantially parallel to longitudinal axis A. A drive shaft 90 comprising metallic wire turns is provided and partially covered by a polymer jacket 92 such that a distal section 96 and a proximal section 97 of the drive shaft 90 are exposed.

The embodiment of FIG. 9 adds a smooth metal liner 94 inside the wire turns of the drive shaft 90 to the embodiment of FIG. 2. One or more features and advantages of the drive shaft 90 and the polymer jacket 92 may be substantially similar to the corresponding features and advantages of the drive shafts and polymer jackets of the embodiments of FIG. 2.

The smooth metal liner 94 is flexible and is not attached to the drive shaft 90. As shown in FIG. 9, the drive shaft 90 further comprises inner proximal and distal stops 100P and 100D. Alternatively, the inner stop of drive shaft 90 may comprise only distal inner stop 100D. Similarly to the inner stops 70P and 70D of the embodiment of FIG. 6, the inner stops 100P and 100D comprise elevations extending from an inner surface of the drive shaft 90 radially inward into the lumen defined by the drive shaft 90. In some cases, inner proximal stop 100P and/or inner distal stop 100D each may comprise more than one elevation, with the several proximal elevations and/or several distal elevations radially spaced from one another about the inner circumference of the corresponding proximal section 97 or distal section 96 of the drive shaft 90. In any such cases, the metal liner 94 is free to move within the drive shaft 90 between inner proximal and/or distal stops 100P and 100D, or between a proximal end of the drive shaft 90 and inner distal stop 100D, in a manner similar to that described above in connection with the polymer jackets and drive shafts of the embodiments of FIGS. 3-5. Metal liner 94 therefore is allowed to move longitudinally within a predetermined distance. If both proximal and distal stops inner 100P and 100D are used, then the distance between proximal and distal stops 100P and 100D may be greater than, or be equal to, the length of the metal liner 94 to define a desired longitudinal length of travel of the metal liner 94. Metal liner thus may provide any or all of the advantages described above with respect to the metal liner 64 of the embodiment of FIG. 6.

Unlike the embodiment of FIG. 8, the drive shaft 80 does not comprise outer proximal and/or distal stops to allow longitudinal travel of the polymer jacket 92 therebetween. In cases in which the polymer jacket 82 is fixed at its proximal end, the polymer jacket does not rotate, and so the drive shaft 90 and the metal liner 94 rotate independently within the polymer jacket 92. Alternatively, the polymer jacket 92 may not be fixed at its proximal end. In such cases, the polymer jacket 92 is free to rotate over the drive shaft 90 during rotation of the drive shaft 90. The polymer jacket 92 of the embodiment of FIG. 9 may provide one or more of the advantages of the polymer jacket of FIGS. 2-8.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. A medical device comprising:
a rotational drive shaft; and
a polymer jacket partially surrounding the rotational drive shaft, a flexible metal liner within a lumen defined by the rotational drive shaft, the flexible metal liner fixed in position both rotationally and longitudinally, wherein the polymer jacket does not rotate in response to rotational motion of the rotational drive shaft and wherein the polymer jacket is fixed in longitudinal position.

2. A medical device comprising:

a rotational drive shaft; and a polymer jacket partially surrounding the rotational drive shaft, wherein the polymer jacket does not rotate in response to rotational motion of the rotational drive shaft and wherein the polymer jacket is fixed in longitudinal position, wherein the flexible metal liner is adapted to move longitudinally independently of the drive shaft, wherein the drive shaft comprises an inner distal stop extending from an inner surface of a distal portion of the drive shaft into the lumen defined by the drive shaft, and wherein the inner distal stop restricts longitudinal movement of the flexible metal liner distally to the inner distal stop.

3. The medical device of claim 2, wherein the drive shaft further comprises an inner proximal stop extending from an inner surface of a proximal portion of the drive shaft into the lumen defined by the drive shaft, and wherein the inner proximal stop and the inner distal stop restrict longitudinal movement of the flexible metal liner between the inner proximal stop and the inner distal stop.

4. A medical device comprising:

a rotational drive shaft; and a polymer jacket partially surrounding the rotational drive shaft, a flexible metal liner within the lumen of the rotational drive shaft, the flexible metal liner fixed in position both rotationally and longitudinally, wherein the polymer jacket is configured to move rotationally and/or longitudinally independently from any rotational motion of the drive shaft.

5. A medical device comprising:

a rotational drive shaft;

a polymer jacket partially surrounding the rotational drive shaft; and a flexible metal liner within the lumen of the rotational drive shaft, wherein the polymer jacket is configured to move rotationally and/or longitudinally independently from any rotational motion of the drive shaft, and wherein the flexible metal liner is adapted to move longitudinally and/or rotationally independently from any rotational motion of the drive shaft, wherein the drive shaft comprises an inner distal stop extending from an inner surface of a distal portion of the drive shaft into the lumen defined by the drive shaft, and wherein the inner distal stop restricts longitudinal movement of the flexible metal liner distally to the inner distal stop.

6. The medical device of claim 5, wherein the drive shaft further comprises an inner proximal stop extending from an inner surface of a proximal portion of the drive shaft into the lumen defined by the drive shaft, and wherein the inner proximal stop and the inner distal stop restrict longitudinal movement of the flexible metal liner between the inner proximal stop and the inner distal stop.

7. The medical device of claim 5, wherein the drive shaft further comprises an outer proximal stop extending radially outwardly from an outer surface of a proximal portion of the drive shaft, and wherein the outer proximal stop and the outer distal stop restrict longitudinal movement of the polymer jacket between the outer proximal stop and the outer distal stop.

8. A rotational atherectomy device comprising:

a prime mover with a prime mover drive shaft operationally connected thereto;

a rotational drive shaft;

an abrading head disposed on the rotational drive shaft a flexible metal liner within the lumen of the rotational drive shaft, the flexible metal liner fixed in position both rotationally and longitudinally; and a polymer jacket partially surrounding the rotational drive shaft, wherein a distal end of the polymer jacket is proximal to the abrading head, wherein the polymer jacket is configured to move rotationally and/or longitudinally independently from any rotational motion of the drive shaft.

9. The rotational atherectomy device of claim 8, wherein the drive shaft comprises an outer distal stop extending radially outwardly from an outer surface of a distal portion of the drive shaft, and wherein the outer distal stop restricts longitudinal movement of the polymer jacket distally to the outer distal stop.

10. The rotational atherectomy device of claim 9, wherein the drive shaft further comprises an outer proximal stop extending radially outwardly from an outer surface of a proximal portion of the drive shaft, and wherein the outer proximal stop and the outer distal stop restrict longitudinal movement of the polymer jacket between the outer proximal stop and the outer distal stop.

11. A rotational atherectomy device comprising:

a prime mover with a prime mover drive shaft operationally connected thereto;

a rotational drive shaft;

an abrading head disposed on the rotational drive shaft;

a flexible metal liner within the lumen of the rotational drive shaft;

a polymer jacket partially surrounding the rotational drive shaft, wherein a distal end of the polymer jacket is proximal to the abrading head, wherein the polymer jacket is configured to move rotationally and/or longitudinally independently from any rotational motion of the drive shaft, and wherein the flexible metal liner is adapted to move longitudinally independently from any rotational motion of the drive shaft, wherein the drive shaft comprises an inner distal stop extending from an inner surface of a distal portion of the drive shaft into the lumen defined by the drive shaft, and wherein the inner distal stop restricts longitudinal movement of the flexible metal liner distally to the inner distal stop.

12. The rotational atherectomy device of claim 11, wherein the drive shaft further comprises an inner proximal stop extending from an inner surface of a proximal portion of the drive shaft into the lumen defined by the drive shaft, and wherein the inner proximal stop and the inner distal stop restrict longitudinal movement of the flexible metal liner between the inner proximal stop and the inner distal stop.

* * * * *